United States Patent [19]

Terry

[11] Patent Number: 5,112,221

[45] Date of Patent: May 12, 1992

[54] EXTRUSION SPRING ARM

[76] Inventor: Sally J. Terry, 137 Beekman St., Plattsburgh, N.Y. 12901

[21] Appl. No.: 551,797

[22] Filed: Jul. 12, 1990

[51] Int. Cl.⁵ ............................................. A61C 3/00
[52] U.S. Cl. ....................................... 433/21; 433/24
[58] Field of Search .............................. 433/18, 21, 24

[56] References Cited

U.S. PATENT DOCUMENTS

| | | | |
|---|---|---|---|
| 3,127,677 | 4/1964 | Schachter | 433/21 |
| 3,237,305 | 3/1966 | Hegedus | 433/21 |
| 3,641,672 | 2/1972 | Kesling | 433/21 |
| 3,793,730 | 2/1974 | Begg et al. | 433/21 |
| 3,835,538 | 9/1974 | Northcutt | 433/24 |
| 4,187,610 | 2/1980 | Ziegler . | |
| 4,580,976 | 4/1986 | O'Meara . | |
| 4,842,514 | 6/1989 | Kesling | 433/21 |
| 4,869,667 | 9/1989 | Vardimon . | |
| 5,035,614 | 7/1991 | Greenfield | 433/21 |

Primary Examiner—Gene Mancene
Assistant Examiner—Michael Lynch
Attorney, Agent, or Firm—Samuel Meerkreebs

[57] ABSTRACT

To aid in the eruption of palatally impacted teeth, an elongated resilient wire, having a loop formed at one end thereof and a coil spring formed at the other end thereof, is attached to an archwire fixed to the patient's mouth, at the coil spring end thereof. An eyelet is bonded to an exposed portion of the impacted tooth, and the loop is attached to the eyelet by an elastic ligature. When the loop is being attached to the eyelet, the resilient arm is moved into a position against the force of the spring so that, when the resilient arm is released, the action of the spring will force the impacted tooth down and out of the palate, into the mouth and laterally, towards a dental arch.

5 Claims, 2 Drawing Sheets

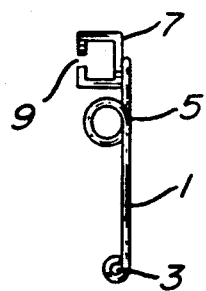
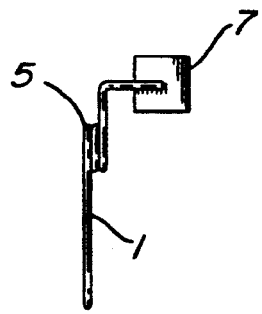
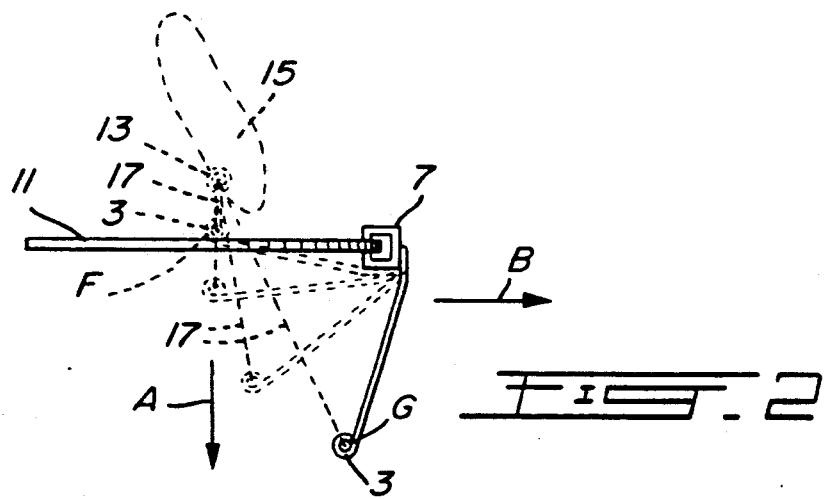
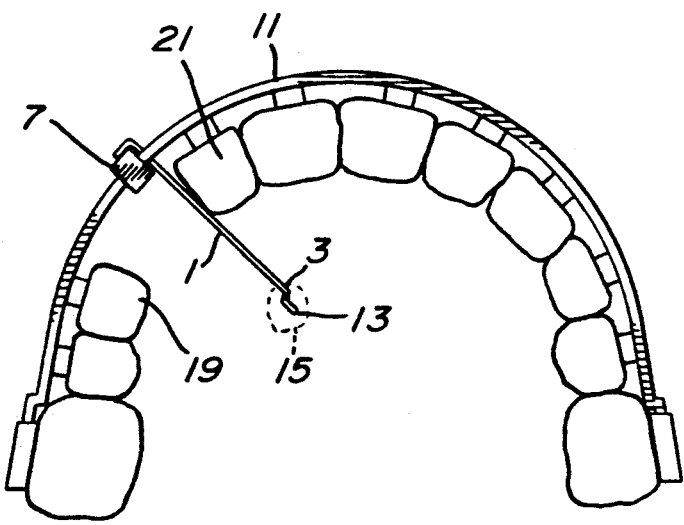

EXTRUSION SPRING ARM

BACKGROUND OF THE INVENTION

1. Field of the Invention

The invention relates to an extrusion spring arm for aiding in the eruption of palatally impacted cuspids. More specifically, the invention relates to such an extrusion spring arm which is mountable on an archwire and activated by an elastic ligature.

2. Description of Prior Art

In the practice of orthodontics, the situation often arises where a patient may have one or both upper cuspids impacted. In cases where the impacted cuspids are palatally positioned, access to the cuspids, and the ability to guide the cuspid into its proper position in the dental arch may be difficult to obtain. What is needed in many, if not all cases, is an extrusive force.

Devices for providing such an extrusive force are known in the prior art as illustrated in, for example, U.S. Pat. No. 4,187,610, Ziegler, Feb. 12, 1980 and U.S. Pat. No. 4,869,667, Vardimon, Sept. 26, 1989.

The Ziegler patent teaches the use of a ligation chain illustrated in FIG. 1 of the patent. One end of the chain has a loop portion 12. In operation, the impacted tooth must be surgically exposed so that all of the crown can be accessed. The loop is then slipped over the tooth and past the crown. The chain is then twisted so that the diameter of the loop is decreased until the diameter of the loop is less than the diameter of the crown. To activate the force to erupt the tooth, an elastic is attached to one end of the eyelet 14 at one end thereof, and to either a band 30 of an adjacent tooth or to an archwire 32. The elastic is, of course, placed under tension. One of the disadvantages of the '610 patent is that the surgeon has to uncover quite a bit of the tooth in order to get the loop 12 over the whole crown. In addition, although the patent states at column 4, lines 4 to 13, that the chain can be subsequently painlessly removed, it seems that the free end of the wire passing around the tooth as the wire is being pulled out could possibly scratch an inside part of the patient.

The Vardimon patent teaches a magnetic approach for the same purpose. Referring to FIG. 1 of the patent, an intra-osseous (bony) magnetic unit 16 is bonded to the tip of the crown of an impacted tooth 12. An intra-oral magnetic unit 18 is disposed in a position to provide magnetic attaction to the magnetic unit 16 whereby to explode the impacted tooth. The intra-oral magnetic unit 18 is mounted on archwire 36 by means of a two-dimensional connector 34. The two-dimensional connector 34 permits adjustment of the intra-oral magnetic unit in that the portion 37 permits sliding along the archwire 36. The disadvantage of this arrangement is that the arch connector in the '667 patent is relatively complex. In addition, the magnetic force is not a flexible force in that it acts only in a single direction.

Also known in the art is U.S. Pat. No. 4,580,976, O'Meara, Apr. 8, 1986, which teaches a spring member 18 mounted on an archwire 12. However, the arrangement in the '976 patent does not relate to exploding or extruding an impacted tooth.

SUMMARY OF INVENTION

It is therefore an object of the present invention to provide an extrusion spring arm for aiding in the eruption of palatally impacted cuspids which overcome the disadvantages of the prior art.

It is a more specific object of the invention to provide such an extrusion spring arm which includes means for mounting the spring arm on an archwire.

It is a still more specific object of the invention to provide such an extrusion spring arm wherein the means for mounting the extrusion spring arm on the archwire permits the position of the extrusion spring arm to be adjusted.

In accordance with the invention there is provided an extrusion spring arm for aiding in the eruption of a palatally impacted teeth of a patient and mountable on an archwire fixed in said patient's mouth, comprising:

an elongated resilient wire having a first end and a second end;

said first end being formed in the shape of loop means;

said second end being formed as spring means;

means for mounting said resilient wire on said archwire;

said spring means being fixedly attached to said means for mounting.

In accordance with a further embodiment of the invention there is provided a method for aiding the eruption of a palatally impacted tooth of a patient, comprising:

surgically exposing a portion of said impacted tooth;

bonding an eyelet to the exposed portion of said impacted tooth;

connecting said eyelet to a looped end of a resilient wire by tying an elastic ligature, at respective ends thereof, to the loop of said looped end and to said eyelet;

the other end of said resilient wire having spring means and being connected to an archwire mounted in said patient's mouth, the resilient wire being moved to a first position against the force of the spring while the elastic ligature is being tied; and releasing said resilient wire;

whereby, the action of the spring means will force the impacted tooth to be moved down and out of the palate, into the mouth of said patient, and laterally, towards a dental arch of said patient.

BRIEF DESCRIPTION OF DRAWINGS

The invention will be better understood by an examination of the following description, together with the accompanying drawings, in which:

FIG. 1A is a side view and FIG. 1B is a front view of a split tube embodiment of the invention;

FIG. 2 is a schematic diagram illustrating how the extrusion spring arm of the present invention operates;

FIG. 3 illustrates the extrusion spring arm in the environment of its usage.

DESCRIPTION OF PREFERRED EMBODIMENTS

Figure 4A:
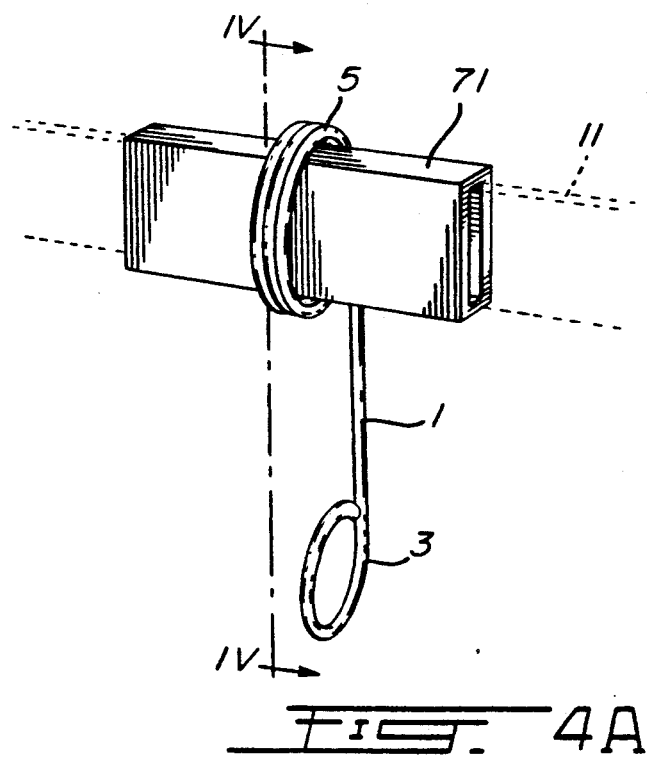
FIG. 4A is a perspective view of a closed tube embodiment of the invention.

Referring to FIGS. 1A and 1B, the extrusion spring arm comprises a resilient wire 1 having a first end and a second end. The first end is formed in the shape of a loop 3 and the second end is formed as a spring means, for example, a coil spring 5.

The second end of the resilient wire is attached to a means for mounting the wire on archwire, for example, a split tubular member 7 having a opening 9. The wire is attached to the tubular member by welding or the like.

Referring now to FIG. 2, the tubular member is mounted on an archwire 11 and, subsequently, crimped into place. An eyelet 13 is bonded to the impacted cuspid 15, and the loop 3 is joined to the eyelet 13 by tying respective ends of an elastic ligature to the eyelet 13 and the loop 3.

The extrusion spring arm is preferably made of 0.018 round resilient wire attached to the crimpable split rectangular tube which may be 4 mm in length and have a wall thickness of 0.015. The archwire which is typically rectangular in cross-section, may have dimensions of 0.018×0.025 or 0.016×0.022, and the internal dimensions of the tubular member are substantially equal to the dimensions of the archwire. The spring arm could be manufactured in different lengths and would include a left model and a right model. The length of the wire could be shortened by bending it as well known in the art.

In operation, an oral surgeon would first uncover a small portion of the crown of the cuspid. From five to seven days later, the patient would return and the surgical packing over the exposed portion of the cuspid would be removed and the eyelet 13 would be bonded to the exposed area of the cuspid. The extrusion spring arm would then be held in place and checked for length and direction. After making minor adjustment to the extrusion spring arm, it would be placed on the archwire and lightly crimped. Once on the archwire, the extrusion spring arm is slid back and forth to make sure it clears all interferences from the lower teeth if possible. It is now firmly crimped in place.

To activate the extrusion spring arm, the eyelet is connected to the loop by tying an elastic ligature, at respective ends thereof, to the eyelet and the loop. Before the ligature is tied, the resilient wire would be moved against the force of the coil spring to a position such as the position "F" in FIG. 2. When the resilient wire is then released after tying, the spring will uncoil so that the loop will tend to move towards the position "G" in FIG. 2. This will force the cuspid to move down and out of the palate, into the mouth, in the direction of the arrow "A" in FIG. 2 and laterally, towards the dental arch; in the direction of the arrow "B" in FIG. 2. Thus, with the extrusion spring arm mounted as illustrated in FIG. 3, the cuspid 15 would be drawn to the space between teeth 19 and 21.

Figure 4B:
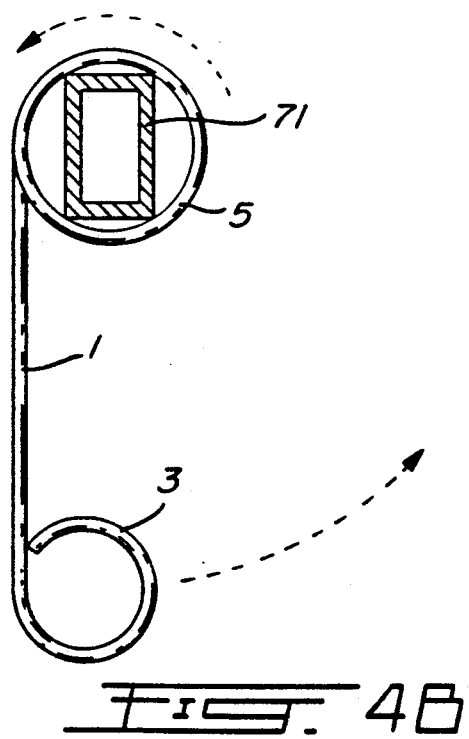
FIG. 4B is a section through IV—IV of FIG. 4A.

In an alternative embodiment, illustrated in FIGS. 4A and 4B, the means for mounting the wire on the archwire comprises a closed tubular member 71. In this embodiment, the coil spring 5 is wound around the tubular member 71.

In the operation of the second embodiment, the extrusion spring arm is mounted on the archwire before the archwire is bent and inserted in the mouth. In all other respects, the procedure for this embodiment is identical to the procedure as above described for the first embodiment.

The tube is made long enough so that there will be enough room on either side of the coil spring to crimp the tube to the archwire when its position has been determined.

In both embodiments, the coil spring is wrapped in a counter clockwise direction. The dimensions of both embodiments are similar.

Although several embodiments have been described, this was for the purpose of illustrating, but not limiting, the invention. Various modifications, which will come readily to the mind of one skilled in the art, are within the scope of the invention as defined in the appended claims.

I claim:

1. An extrusion spring arm for aiding in the eruption of a palatally impacted tooth of a patient and mountable on an archwire fixed in said patient's mouth, comprising:
   an elongated resilient wire having a first end and a second end;
   said first end being formed in the shape of loop means;
   said second end being formed as spring means;
   said first and second ends being in substantial alignment;
   means for mounting said resilient wire on said archwire;
   said spring means being fixedly attached to said means for mounting;
   wherein said spring means comprises a coil spring;
   and wherein said means for mounting comprises a tubular member, said tubular member comprising a closed tube;
   said coil spring surrounding said closed tube and being fixedly attached thereto.

2. An extrusion spring arm as defined in claim 1 wherein said closed tube comprises an elongated member having a length;
   said coil spring surround said tube centrally of the length thereof.

3. An extrusion spring arm as defined in any one of claims 1 or 2 wherein said archwire has cross-sectional dimensions;
   the inside dimensions of said tube being substantially equal to the cross-sectional dimensions of said archwire.

4. An extrusion spring arm as defined in any one of claims 1 or 2 wherein said archwire has cross-sectional dimensions of height and thickness;
   the inside diameter of said tube members being substantially equal to the cross-sectional dimensions of said archwire.

5. A method for aiding the eruption of a palatally impacted tooth of a patient, comprising:
   surgically exposing a portion of said impacted tooth;
   bonding an eyelet to the exposed portion of said impacted tooth;
   connected said eyelet to a looped end of a resilient wire by tying an elastic ligature, at respective ends thereof, to the loop of said looped end and to said eyelet;
   the other end of said resilient wire having spring means and being connected to an archwire mounted in said patient'mouth, the resilient wire being moved to a first position against the force of the spring while the elastic ligature is being tied; and
   releasing said resilient wire;
   whereby the action of the spring means will force the impacted tooth to be moved down and out of the palate, into the mouth of said patient, and laterally, towards a dental arch of said patient.

* * * * *